United States Patent [19]

Burkinshaw

[11] Patent Number: 5,702,465
[45] Date of Patent: Dec. 30, 1997

[54] PATELLA PROSTHESIS HAVING ROTATIONAL AND TRANSLATIONAL FREEDOM

[75] Inventor: Brian D. Burkinshaw, Pflugerville, Tex.

[73] Assignee: Sulzer Orthopedics Inc., Austin, Tex.

[21] Appl. No.: 648,222

[22] Filed: May 13, 1996

[51] Int. Cl.$^6$ ............................................. A61F 2/38
[52] U.S. Cl. ................................................ 623/20; 623/18
[58] Field of Search ............................... 623/16, 18, 20

[56] References Cited

U.S. PATENT DOCUMENTS

| | | | |
|---|---|---|---|
| 4,085,466 | 4/1978 | Goodfellow et al. | 3/1.91 |
| 4,219,893 | 9/1980 | Noiles | 3/1.911 |
| 4,470,158 | 9/1984 | Pappas et al. | 3/1.911 |
| 4,950,297 | 8/1990 | Elloy et al. | 623/20 |
| 4,979,957 | 12/1990 | Hodorek | 623/20 |
| 5,330,533 | 7/1994 | Walker | 623/20 |

Primary Examiner—David Isabella
Assistant Examiner—John M. Black
Attorney, Agent, or Firm—Richard L. Robinson

[57] ABSTRACT

A patellar prosthesis includes an articulation component having a prosthetic articulation surface and a base component for fixation to resected patellar bone. Each of the articulation and base components include planar bearing surfaces in sliding engagement. The base component includes a fixed pin extending perpendicularly from its respective planar bearing surface. The articulation component includes an elongate groove in its respective planar bearing surface. The pin and groove have complementary wall profiles that provide for an elastic snap-retention of the pin within the groove. The articulation component is free to rotate about the axis of the pin received within the groove, and is free to translate parallel to the planar bearing surfaces, limited by the length of the groove. The articulation component enjoys only one rotational degree of freedom, and only two translational degrees of freedom. For any determined rotational orientation, translation is limited to one degree of freedom, parallel to the length of the groove. The articulation component is free to rotate about the pin at any point along the length of the groove.

10 Claims, 3 Drawing Sheets

PATELLA PROSTHESIS HAVING ROTATIONAL AND TRANSLATIONAL FREEDOM

BACKGROUND OF THE INVENTION

1. Field of the Invention

The present invention relates generally to implantable orthopedic prostheses for replacing the natural articulating surfaces of bone joints, and more particularly to implantable patellar prostheses for replacing the natural articulation surface of the patella at the knee joint.

2. Background of the Related Art

The human knee joint involves three bones: the femur, the tibia and the patella, each having smooth articulation surfaces arranged for articulation on an adjacent articulation surface of at least one other bone. The femur includes at its distal extremity an articulation surface having medial and lateral convex condyles separated posteriorly by an intercondylar groove running generally in the anterior-posterior direction, the condyles joining at the distal-anterior face of the femur to form a patellar surface having a shallow vertical groove as an extension of the intercondylar groove. The patella includes on its posterior face an articulation surface having a vertical ridge separating medial and lateral convex facets, which facets articulate against the patellar surface of the femur and against the medial and lateral condyles during flexion of the knee joint, while the vertical ridge rides within the intercondylar groove to prevent lateral displacement of the patella during flexion. The tibia includes at its proximal end an articulation surface having medial and lateral meniscal condyles that articulate against the medial and lateral condyles, respectively, of the femur. The mutually engaging articulation surfaces of the femur and the patella together form, functionally, the patellofemoral joint, and the mutually engaging articulation surfaces of the femur and tibia together form, functionally, the tibiofemoral joint, which two functional joints together form the anatomical knee joint.

Because of disease or trauma, all or part of one or more of the articulation surfaces of the knee joint may fail to perform properly, requiring replacement of the defective natural articulation surface with a prosthetic articulation surface provided by an implantable prosthesis. To accommodate defects of varying scope, while permitting healthy portions of the knee joint to be conserved, a range of types of orthopedic implants is available. The range extends from total knee prosthesis systems for replacing the entire articulation surface of each of the femur, tibia and patella, to less comprehensive systems for replacing only the tibiofemoral joint, or only one side (medial or lateral) of the tibiofemoral joint, or only the patellofemoral joint.

The present invention is particularly useful for knee joint replacement surgery and prosthetic knee joint systems in which the natural articulation surface of the patella is replaced by a prosthetic articulation surface. Such replacements are often accomplished by surgically resecting the patella to remove the posterior portion of the bone, leaving a planer bony surface to which a patellar prosthesis "button" is affixed. The patellar prosthesis "button" provides a prosthetic articulation surface on the patella for articulation against a prosthetic patellar articulation surface of the femur. The patellar prosthesis usually has an articulation surface comprising a biocompatible synthetic polymer material, such as ultra high molecular weight polyethylene, that is either an integral part of an all-polyethylene prosthesis or carried by a metal backing or base. The patellar prosthesis has an affixation surface affixed to the resected bony surface of the patella, usually with bone cement, opposite the artificial articulation surface. The affixation surface may also be a porous surface to promote ingrowth of bone, and may include pins or other extensions received within corresponding holes or recesses cut into the resected bony surface of the patella to provide additional fixation and stability.

To provide proper anatomic function of the knee joint following surgery, it is important that the prosthetic articulation surfaces be placed accurately during surgery to provide proper alignment and spacing therebetween. Placing and orienting the patellar prosthesis precisely on the resected bony surface during surgery can be difficult sometimes. If placed properly, the prosthetic articulation surface of the patella will track the intercondylar groove and anterior patellar surface of the femoral prosthesis while the patellar tendon is in tension during flexion and extension of the joint. If placed improperly, particularly with respect to its location in the medial-lateral direction, the prosthetic articulation surface of the patella may fail to track accurately, resulting in recurrent dislocation of the patella or accelerated wear of the articulation surface, or both. If the prosthetic articulation surface of the patella is configured for congruent sliding contact with the femoral prosthesis or is otherwise configured for simulating the action of the natural articulation surface by tracking the intercondylar groove, the angular orientation of the patellar prosthesis on the resected bony surface of the patella is also important. Improper angular placement during surgery may result in the same problems discussed above concerning medial-lateral misplacement.

It is known in the art to alleviate the problems associated with angular misplacement of the patellar prosthesis during surgery by providing a two-part patellar prosthesis including a first part having an articulation surface and a second part having an affixation surface for affixation to the resected bony surface of the patella, in which the first and second parts are secured together by means permitting rotation of the two parts relative to each other about a fixed axis perpendicular to the resected planar surface of the patella. Such construction allows for some error in angular orientation during affixation of the second part of the prosthesis to the resected patella during surgery. After surgery the first part of the prosthesis will rotate relative to the second part into proper angular orientation under the influence of the forces imparted by the patellar tendon as the prosthetic articulation surface of the patella engages the femoral articulation surfaces during flexion and extension of the knee.

Providing an implantable patellar prosthesis that alleviates the problems associated with medial-lateral and angular misplacement of the patellar prosthesis during surgery would be desirable. This and other desirable advantages are provided by the present invention.

SUMMARY OF THE INVENTION

According to one aspect of the invention, an implantable patellar prosthesis for replacing the natural articulation surface of a patella includes a base component having a fixation surface for fixation to patellar bone and an articulation component having a prosthetic articulation surface. Means are included for connecting the articulation component to the base component to permit motion of the articulation component relative to the base component while limiting the relative motion to one rotational degree of freedom and two translational degrees of freedom.

It is an object of the present invention to provide an implantable patellar prosthesis that alleviates problems associated with medial-lateral and angular misplacement of the patellar prosthesis on the resected patella during surgery.

Other objects and advantages of the present invention will be apparent from the following descriptions of a preferred embodiment referencing the drawings.

DETAILED DESCRIPTION OF THE PREFERRED EMBODIMENT

Figure 1:
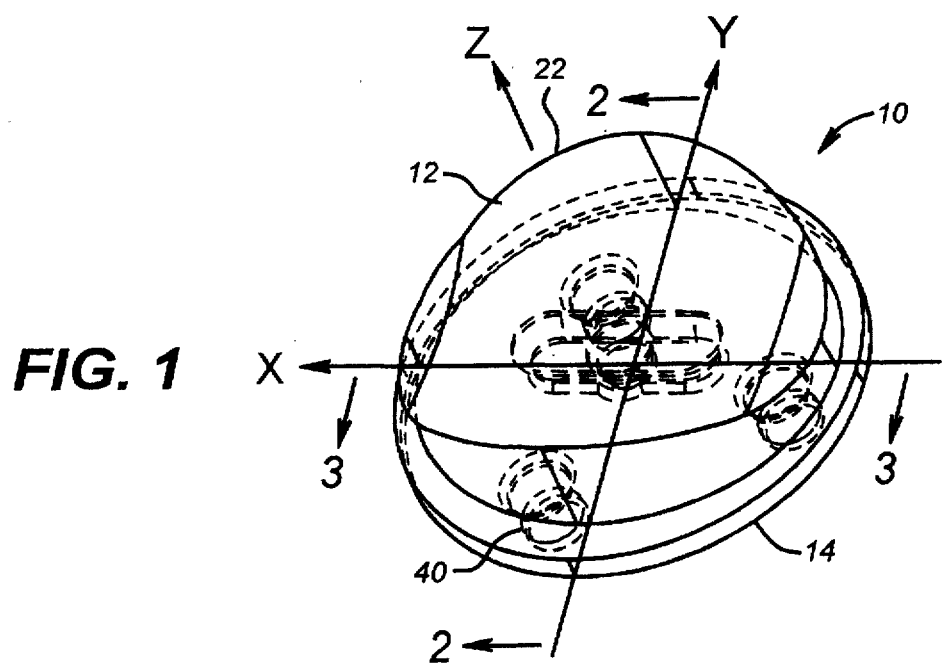
FIG. 1 is a perspective view of an embodiment of an implantable patellar prosthesis for replacing the natural articulation surface of a patella.
Figure 2:
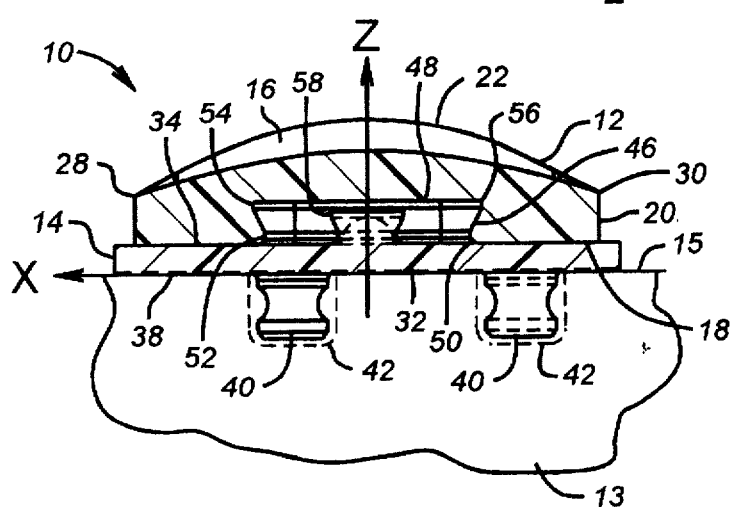
FIG. 2 is a cross-sectional view of the prosthesis of FIG. 1, taken along plane 2—2 and viewed in the direction of the arrows.
Figure 3:
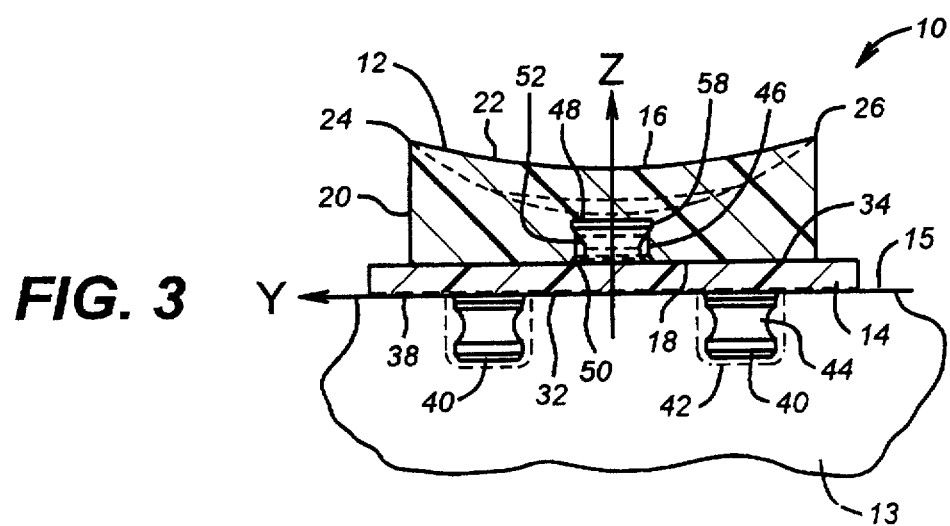
FIG. 3 is a cross-sectional view of the prosthesis of FIG. 1, taken along plane 3—3 and viewed in the direction of the arrows.
Figure 5:
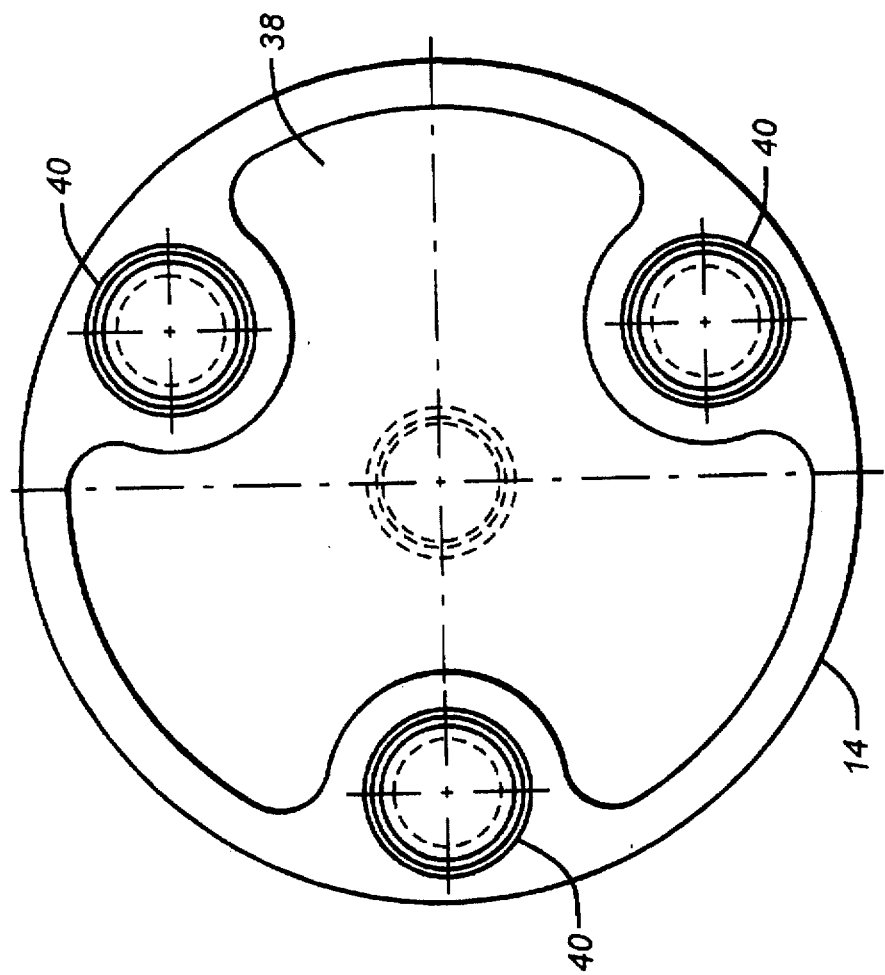
FIG. 5 is a bottom view of the base component of FIG. 4.
Figure 4:
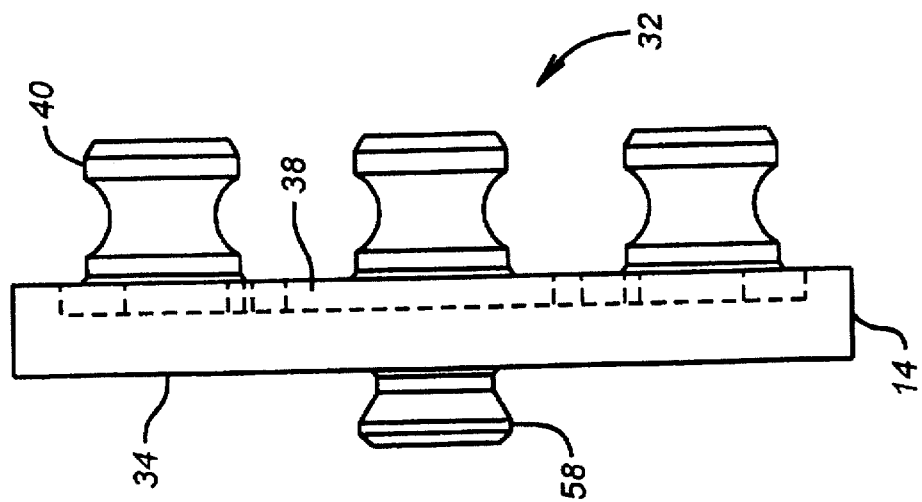
FIG. 4 is a side view of a base component of the prosthesis of FIG. 1.
Figure 8:
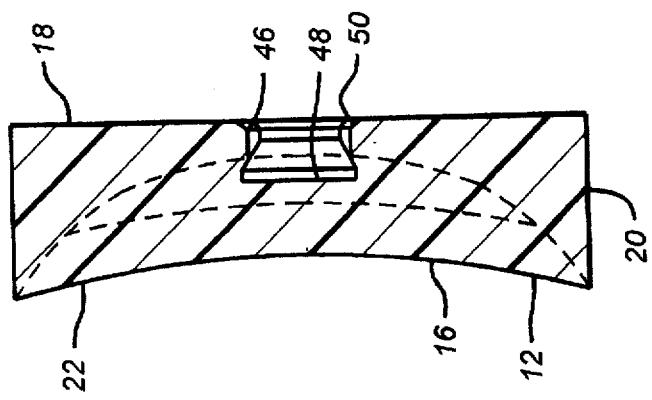
FIG. 8 is a cross-sectional view of the articulation component of FIG. 6 taken along plane 8—8 and viewed in the direction of the arrows.
Figure 6:
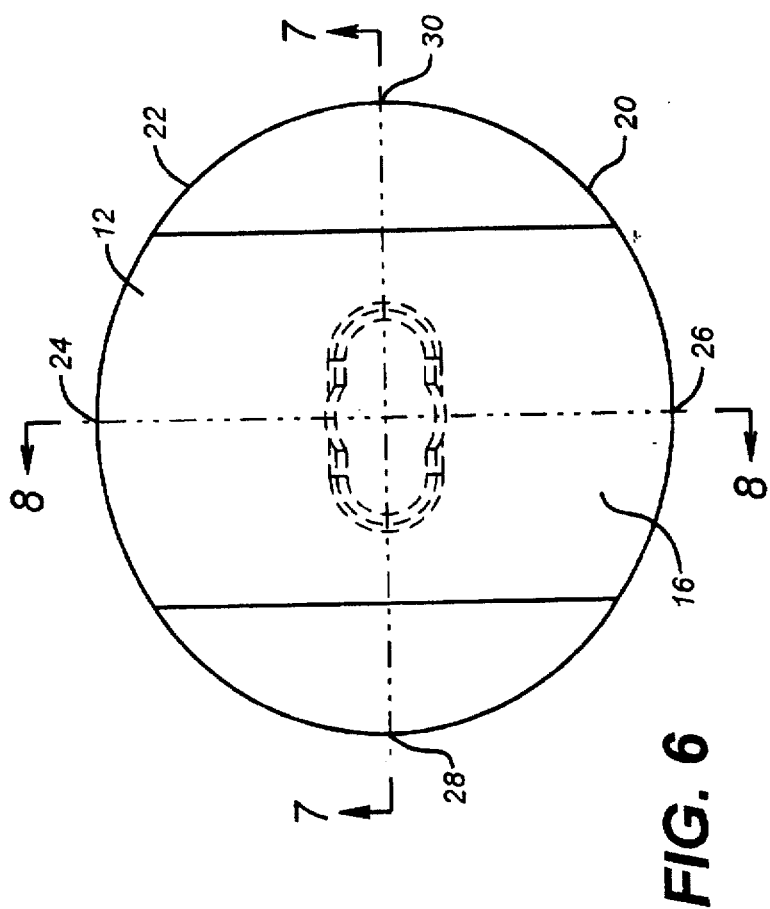
FIG. 6 is a top view of an articulation component of the prosthesis of FIG. 1.
Figure 7:
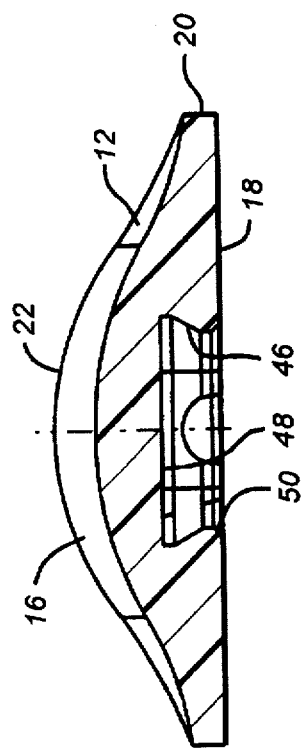
FIG. 7 is a cross-sectional view of the articulation component of FIG. 6 taken along plane 7—7 and viewed in the direction of the arrows.

Referring to FIGS. 1–3, there is illustrated an implantable patellar prosthesis 10 having an articulation component 12 and a base component 14 shown relative to mutually orthogonal reference axes X, Y and Z. When prosthesis 10 is implanted, reference axes X, Y and Z correspond, generally, to well known and accepted anatomical directional terms. The X axis extends generally in the medial-lateral direction, the Y axis extends generally in the inferior-superior direction, and the Z axis extends generally in the posterior-anterior direction. If the prosthesis 10 were implanted on the left patella of a human patient, the ends of each of the X, Y, and Z axes marked with an arrowhead would point generally in the medial, superior and posterior directions, respectively. During surgery, the patella is resected in a plane generally perpendicular to the anterior-posterior direction to remove a posterior portion of the patellar bone, leaving a resected planar bony surface 15. When prosthesis 10 is implanted, the Z axis lies perpendicular to the resected planar bony surface 15 of a patella 13, and the X and Y axes lie parallel to the resected planar bony surface 15.

Articulation component 12 is constructed of a biocompatible material having desirable wear and bearing friction properties, such as ultra-high molecular weight polyethylene. Articulation component 12 includes and is bounded and defined by an articulation surface 16, a planar bearing surface 18 generally perpendicular to the Z axis and spaced from the articulation surface 16, and a perimetrical wall 20 that is generally parallel to the Z axis and that connects the articulation surface 16 and the planar bearing surface 18. In the plane defined by the X and Y axes, perimetrical wall 20 is generally elliptical, with the major axis oriented generally in the medial-lateral direction, along the X axis. Articulation surface 16, in the preferred embodiment shown, is a hyperbolic paraboloid, also known as a "saddle" shape, in which the intersection of the surface 16 and perimetrical wall 20 defines an undulating edge 22. Points 24 and 26 at opposite ends of the "saddle" designate the locations at which undulating edge 22 is at its maximum spacing from planar bearing surface 18. Points 24 and 26 are on the minor axis of elliptical perimetric wall 20, and are disposed relative to each other generally in the inferior-superior direction, along the Y axis. Points 28 and 30 at opposite sides of the "saddle" designate the locations at which undulating edge 22 is at its minimum spacing from planar bearing surface 18. Points 28 and 30 are on the major axis of elliptical perimetric wall 20, and are disposed relative to each other generally in the medial-lateral direction, along the X axis. Articulation surface 16, so configured, ideally provides congruent sliding contact over an extensive range of articulation between articulation component 12 and the patellar articulation surface of a femoral prosthesis component (not shown) at the patellofemoral joint. Undulating edge 22 at points 24 and 26 at the high ends of the "saddle" functionally defines a ridge that can track the intercondylar groove of the femoral component during flexion and extension of the knee joint.

Base component 14 is constructed of a biocompatible material having desirable wear, bearing friction, and bone engaging properties. Examples of such a material are titanium, titanium alloys, zirconia ceramics, aluminum oxide ceramics, and cobalt chromium alloys. Base component 14 includes and is bounded and defined by a fixation surface 32 for engaging patellar bone 15, a planar bearing surface 34 generally perpendicular to the Z axis and spaced from the fixation surface 32, and a perimetrical wall 36 that is generally parallel to the Z axis and that connects the fixation surface 32 and the planar bearing surface 34. In the plane defined by the X and Y axes, perimetrical wall 36 is generally circular. Fixation surface 32 includes a generally planar surface portion 38 for engaging resected planar bony surface 13 generally parallel thereto, directly or via a mantle of bone cement. Planar surface portion 38 can include surface texturing to promote osseointegration of fixation component 14. Such surface texturing can be provided by a coating of hydroxyapatite or other ceramics, or porous metal, for example. Such coatings can be applied by plasma spraying of powdered material or, for porous metal coatings, by sintering powdered metal or beads. Suitable metals include titanium and its alloys and cobalt chromium alloys. Other materials and methods for providing a surface that favors osseointegration are well known in the art. Fixation surface 32 also includes three pins, or pegs, 40, evenly and symmetrically spaced, extending integrally from fixation surface 32 generally in the anterior direction, parallel to the Z axis. Pins 40 are received in correspondingly shaped bores 42 in patella 15. Pins 40 are provided with a waist 44 of a reduced diameter, and alternatively can be straight or provided with other macro-textured surface profiles, to enhance fixation of fixation component 14 to patellar bone 15, either by bone cement or osseointegration.

Articulation component 12 includes an elongate groove 46 that opens to planar bearing surface 18 and oriented longitudinally parallel to a line drawn between points 28 and 30 at the low points of perimetrical wall 20. When articulation component 12 is implanted, groove 46 extends longitudinally generally in the medial-lateral direction, along the X axis. Groove 46 is of constant and similar width at its base 48 and at its opening 50, but is of reduced width therebetween, presenting a narrowed throat 52 in transverse cross-section. Groove 46 is arcuate at each end 54 and 56, subtending an angle of about 180 degrees between each side of groove 46. Each arcuate end 54 and 56 is similar in profile to the sides of groove 46, presenting a like narrowed throat 52 when viewed in cross-section.

Fixation component 14 includes a pin, or peg, 58, centered on and extending integrally from planar bearing surface 34 in the posterior direction, along the Z. axis. Pin 58 is circular in cross-section, but with a diameter that varies in the profile generally complementarily to the profile of groove 46.

Articulation component 12 and fixation component 14 are configured to engage each other in a snap-retaining relationship, such that the opening of groove 46 deforms elastically under pressure to permit entry of pin 58, and afterwards elastically rebounds to engage and to retain pin 58. When so retained, groove 46 can rotate and translate relative to pin 58. When articulation component 12 and fixation component 14 are so engaged, planar bearing surface 18 of articulation component 12 lies in intimate parallel engagement with planar bearing surface 34 of fixation component 14. The width of groove 46, relative to the diameter of pin 58, is such as to preclude substantial movement of articulation component 12 transversely to groove 46 in the plane defined by axes X and Y, whereas articulation component 12 can translate freely in that same plane along the length of groove 46 between the arcuate ends 54 and 56 of groove 46. Because pin 58 is fixed relative to planar bearing surface 34, such movement results in parallel sliding translation of planar bearing surface 18 relative to planar bearing surface 34. It follows that articulation component 12 can rotate about an axis at and defined by pin 58 at any point along the length of groove 46, resulting in rotational sliding of bearing surface 18 relative to bearing surface 34.

As described below, the articulation component is said to enjoy several degrees of freedom of movement relative to the base component. The term "degree of freedom" is used in its ordinary engineering sense to mean freedom of a component to rotate about or translate along a line that is parallel to one axis of a three-axis Cartesian coordinate system fixed in orientation relative to the reference component. The freedom to rotate about such a line comprises one degree of rotational freedom, and the freedom to translate along such a line comprises one translational degree of freedom. A component can enjoy a maximum of six degrees of freedom, in which case the component can rotate about any axis and can translate along any axis. Essentially, a component with six degrees of freedom is unconstrained by any other component.

Relative to base component 14, articulation component 12 enjoys one, and only one, rotational degree of freedom. Articulation component is constrained from rotating about the X or Y axes by the planar engagement of bearing surface 18 against bearing surface 34. Articulation component 12 may freely rotate about the Z axis, however.

Again relative to base component 14, articulation component 12 enjoys only two translational degrees of freedom. Articulation component 12 is constrained against translation in the Z axis by the engagement of bearing surface 18 against bearing surface 34, and by the axially retentive engagement of pin 58 and groove 46. It should be noted that because of the elongate form of groove 46, translation of articulation component 12 in the plane defined by the X and Y axes is limited by the rotational orientation of articulation component 12 relative to fixation component 14. Thus, for any given rotational orientation, only one translational degree of freedom is afforded. Conversely, rotation is not limited by the translational position, because articulation component 12 can rotate about the axis of pin 58 regardless of the translational position of groove 46 relative to pin 58.

The result, and primary benefit, of the configuration described herein is that the articulation component 12 is free to translate and rotate to its correct and optimum location and orientation relative to the femoral component, despite misplacement of the fixation component relative to the patella, with respect to both rotational orientation and medial-lateral position.

What is claimed is:

1. An implantable patellar prosthesis for replacing the natural articulation surface of a patella, comprising:
   a base component having a fixation surface for fixation to patellar bone;
   an articulation component having a prosthetic articulation surface; and
   means for connecting said articulation component to said base component to permit motion of said articulation component relative to said base component while limiting said relative motion to one rotational degree of freedom and two translational degrees of freedom.

2. The implantable patellar prosthesis of claim 1, in which said means for connecting includes a first generally planar bearing surface on said articulation component and a second generally planar bearing surface on said base component, said first and second planar bearing surfaces being generally parallel and disposed for mutual sliding translation.

3. The implantable patellar prosthesis of claim 2, in which said one rotational degree of freedom is about an axis generally perpendicular to said second generally planar bearing surface.

4. The implantable patellar prosthesis of claim 2, in which said two translational degrees of freedom are in a plane generally parallel to said second generally planar bearing surface.

5. The implantable patellar prosthesis of claim 3, in which said two translational degrees of freedom are in a plane generally parallel to said second generally planar bearing surface.

6. The implantable patellar prosthesis of claim 3, in which said axis of said one rotational degree of freedom is fixed relative to said base component.

7. The implantable patellar prosthesis of claim 3, in which said axis of said one rotational degree of freedom is translatable relative to said articulation component.

8. The implantable patellar prosthesis of claim 6, in which said axis of said one rotational degree of freedom is translatable relative to said articulation component.

9. The implantable patellar prosthesis of claim 7, in which translation of said axis of said one rotational degree of freedom is limited substantially to one translational degree of freedom.

10. The implantable patellar prosthesis of claim 1, in which for any determined rotational orientation of said articulating component relative to said base component, said articulation component is limited to one translational degree of freedom.

* * * * *